(12) United States Patent
Patel et al.

(10) Patent No.: US 12,225,903 B2
(45) Date of Patent: Feb. 18, 2025

(54) SYNERGISTIC CLEANING DISINFECTANT SOLUTION WITH ENHANCED STABILITY, AND METHODS OF USING THE SAME

(71) Applicant: Diversey, Inc., Fort Mill, SC (US)

(72) Inventors: Bhavesh Kantilal Patel, Thane (IN); Kedar Pandurang Chaudhari, Thane (IN); Henry von Rege, Alzey (DE)

(73) Assignee: DIVERSEY, INC., Fort Mill, SC (US)

( * ) Notice: Subject to any disclaimer, the term of this patent is extended or adjusted under 35 U.S.C. 154(b) by 663 days.

(21) Appl. No.: 17/617,716

(22) PCT Filed: Jun. 8, 2020

(86) PCT No.: PCT/US2020/036592
§ 371 (c)(1),
(2) Date: Dec. 9, 2021

(87) PCT Pub. No.: WO2020/251885
PCT Pub. Date: Dec. 17, 2020

(65) Prior Publication Data
US 2022/0232828 A1    Jul. 28, 2022

(30) Foreign Application Priority Data

Jun. 12, 2019 (IN) .............................. 201911023296

(51) Int. Cl.
| | | |
|---|---|---|
| *A01N 37/40* | (2006.01) | |
| *A01N 25/04* | (2006.01) | |
| *A01N 25/30* | (2006.01) | |
| *A01N 31/02* | (2006.01) | |
| *A01N 37/36* | (2006.01) | |
| *A01P 1/00* | (2006.01) | |

(52) U.S. Cl.
CPC ............. *A01N 37/40* (2013.01); *A01N 25/04* (2013.01); *A01N 25/30* (2013.01); *A01N 31/02* (2013.01); *A01N 37/36* (2013.01); *A01P 1/00* (2021.08)

(58) Field of Classification Search
None
See application file for complete search history.

(56) References Cited

U.S. PATENT DOCUMENTS

| | | | |
|---|---|---|---|
| 3,589,859 A | 6/1971 | Foroulis | |
| 6,867,233 B2* | 3/2005 | Roselle | A23L 3/3508 514/561 |
| 6,936,579 B2* | 8/2005 | Urban | C11D 3/2086 510/273 |
| 9,555,018 B2* | 1/2017 | Consalo | C12N 1/20 |

FOREIGN PATENT DOCUMENTS

| | | |
|---|---|---|
| CN | 106386899 A | 2/2017 |
| WO | 01/64035 A2 | 9/2001 |
| WO | 2015/198265 A2 | 12/2015 |

OTHER PUBLICATIONS

International Search Report of Application No. PCT/US2020/036592 mailed Aug. 31, 2020; 3 pages.
Rahn et al., "Effect of Increase in Acidity on Antiseptic Efficiency," Industrial & Engineering Chemistry, vol. 070, No. 69, Jan. 1, 1944, 4 pages.

* cited by examiner

*Primary Examiner* — Brian J Davis
(74) *Attorney, Agent, or Firm* — LORENZ & KOPF, LLP

(57) ABSTRACT

A method of cleaning and disinfecting a surface comprises producing a diluted cleaning disinfectant solution from a concentrated cleaning disinfectant solution, and contacting the surface with the diluted solution. A concentrated cleaning disinfectant solution is stable at freezing temperatures and comprises antimicrobial acid, surface cleaning acid, solubilizing agent, hydrotrope, and surfactant. The antimicrobial acid comprises a synergistic combination of (i) salicylic acid, derivative of salicylic acid, or a combination thereof, and (ii) gluconic acid, derivative of salicylic acid, or a combination thereof. The surface cleaning acid comprises at least one acid selected from mineral acid, methane sulfonic acid, formic acid, or sulfonic acid having an alkyl group with no greater than three carbon atoms. The surfactant selected from anionic surfactant, non-ionic surfactant, or a mixture thereof.

20 Claims, No Drawings

SYNERGISTIC CLEANING DISINFECTANT SOLUTION WITH ENHANCED STABILITY, AND METHODS OF USING THE SAME

CROSS-REFERENCE TO RELATED APPLICATION

This application is a National Phase of PCT International Application No. PCT/US2020/036592, filed on June 8, 2020, which claims priority to Indian Provisional Application No. 201911023296, filed on Jun. 12, 2019, the content of these patent applications are incorporated herein by reference.

TECHNICAL FIELD

The present application relates to a cleaning disinfectant solution that is stable at freezing temperatures, and a method for using such cleaning disinfectant solution for cleaning and disinfecting surface.

BACKGROUND

Food contact surfaces are any surface that may come into contact with food products during production, processing or packaging. Cleaning and disinfecting food contact surfaces is one of the most important steps to prevent foodborne illness. Food residues on food contact surfaces and equipment can provide an ideal environment for the growth of disease-causing microbials.

Conventionally, the method of cleaning and disinfecting food contact surfaces comprises cleaning the surfaces, followed by rinsing the surfaces, then disinfecting the surfaces and finally rinsing the disinfectant from the surfaces. Any residue disinfectant must be entirely removed from the surfaces, in order to eliminate any risk of transferring the residue disinfectant to food or beverage products that contact the surfaces after the surfaces have been cleaned.

Furthermore, certain antimicrobial additives tend to crystallize at reduced temperatures making such compositions instable, particularly when in transport when they may experience lower temperatures.

There remains a need in the art for cleaning disinfectant solutions that are capable of both cleaning and disinfecting surfaces, and that remain stable even when subjected to reduced temperatures.

SUMMARY

In one aspect, a concentrated cleaning disinfectant solution is stable at freezing temperatures and suitable for cleaning and disinfecting a surface. The concentrated cleaning disinfectant solution includes antimicrobial acid comprising a synergistic combination of (i) gluconic acid, derivative of gluconic acid, or a combination thereof and (ii) salicylic acid, derivative of salicylic acid, or a combination thereof. The concentrated cleaning disinfectant solution further comprises surface cleaning acid, solubilizing agent, hydrotrope, and surfactant. The surface cleaning acid comprises at least one acid selected from mineral acid, methane sulfonic acid, formic acid, or sulfonic acid having an alkyl group with no greater than three carbon atoms. The surfactant is selected from anionic surfactant, non-ionic surfactant, or a mixture thereof.

In another aspect, a method of cleaning and disinfecting a surface comprises producing a diluted cleaning disinfectant solution from aforementioned concentrated cleaning disinfectant solution, and contacting the surface with the diluted solution. The surface may be a surface of industrial process equipment, or a food contact surface, or both.

Other aspects and embodiments will become apparent upon review of the following description.

DETAILED DESCRIPTION

The present disclosure generally relates to a concentrated cleaning disinfectant solution that is stable at freezing temperatures and suitable for cleaning and disinfecting a surface. The concentrated cleaning disinfectant solution comprises a synergistic combination of (i) gluconic acid, derivative of gluconic acid, or a combination thereof and (ii) salicylic acid, derivative of salicylic acid, or a combination thereof, to improve its cleaning and disinfecting performance of the surface. The concentrated cleaning disinfectant solution further comprises a specific mixture of solubilizing agents, so that the concentrated solution remains stable at low temperatures, in particular, temperatures at or below 0° C.

The terms "comprise(s)," "comprising," "include(s)," "including," "having," "has," "contain(s)," "containing," and variants thereof, as used herein, are open-ended transitional phrases, terms, or words that are meant to encompass the items listed thereafter and equivalents thereof as well as additional items. Where the term "comprising" is used, the present disclosure also contemplates other embodiments "comprising", "consisting of", or "consisting essentially of" elements presented herein, whether explicitly set forth or not.

As used in the specification and in the appended claims, the singular forms "a", "an", and "the" include plural referents unless the context clearly indicates otherwise. For example, reference to "an antimicrobial" includes a plurality of such antimicrobials.

Any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The amount of a component in the solution as disclosed herein is expressed as "% by weight" or "wt %", which refers to the percentage of the component's weight in the total weight of the solution. Unless indicated otherwise, all concentrations are expressed as weight percentage concentrations.

The term "effective amount" refers to an amount effective that would achieve a desired effect or result. For example, an effective amount of a disinfectant composition may refer to the amount of such composition to achieve a level of antimicrobial activity, which can be measured with a standardized test known in the art. An effective amount of a disinfectant composition may be determined by known methods and may vary according to factors such as the microbial strains, test media, temperature, and other conditions.

The term "substantially free", "free", "substantially no", or "no" refers to a disinfectant composition that does not contain a particular compound, or to which a particular compound has not been added to the disinfectant composition. Should the particular compound be present through contamination, the amount of such particular compound shall be less than 0.5% by weight, preferably less than 0.1% by weight.

As used herein, "antimicrobial" means a compound or solution intended to destroy, deter, and/or render bacterial species, fungi and viruses harmless. As a non-limiting example, "antimicrobial" may be an agent that kills microorganisms or stops their growth.

The concentrated cleaning disinfectant solution of the present disclosure is stable at a freezing temperature and comprises:
  antimicrobial acid comprising a synergistic combination of (i) gluconic acid, derivative of gluconic acid, or a combination thereof and (ii) salicylic acid, derivative of salicylic acid, or a combination thereof;
  surface cleaning acid comprising at least one acid selected from mineral acid, methane sulfonic acid, formic acid, or sulfonic acid having an alkyl group with no greater than three-carbon atoms;
  solubilizing agent;
  hydrotrope; and
  surfactant selected from anionic surfactant, non-ionic surfactant, or a mixture thereof.

Antimicrobial Acid

The antimicrobial acid comprises a synergistic combination of (i) gluconic acid, derivative of gluconic acid, or a combination thereof and (ii) salicylic acid, derivative of salicylic acid, or a combination thereof.

The term "derivative of gluconic acid", as used herein, refers to oligomer of gluconic acids that is degradable to release gluconic acids, or salt of gluconic acid, or any combination thereof. The oligomer of gluconic acids may have, on average, from about 2 to about 10 repeat units, from about 3 to about 8 repeat units, or from about 4 to about 6 repeat units.

The term "derivative of salicylic acid", as used herein, refers to oligomer of salicylic acids that is degradable to release salicylic acids, or salt of salicylic acid, or any combination thereof. The oligomer of salicylic acids may have, on average, from about 2 to about 10 repeat units, from about 3 to about 8 repeat units, or from about 4 to about 6 repeat units.

In some embodiments of present disclosure, the antimicrobial acid is substantially free of any other carboxylic acids such as fumaric acid, citric acid, lactic acid, oxalic acid, maleic acid, acetic acid, tartaric acid, malic acid, succinic acid, propionic acid, glycolic acid, benzoic acid, and the like.

In some embodiments, the antimicrobial acid consists essentially of, or consists of, a synergistic combination of (i) gluconic acid, derivative of gluconic acid, or a combination thereof and (ii) salicylic acid, derivative of salicylic acid, or a combination thereof.

In some embodiments, the concentrated cleaning disinfectant comprises the antimicrobial acid in an amount of at least 1%, at least 2%, at least 3%, at least 4%, at least 5%, or at least 10% by weight; and/or no more than 15%, no more than 12%, no more than 11%, no more than 5%, or no more than 4% by weight based on total weight of the concentrated solution.

In some embodiments, the concentrated cleaning disinfectant comprises antimicrobial acid in an amount of from about 1% to about 15%, from about 1.5% to about 15%, from about 1.5% to about 12%, from about 1.5% to about 4%, from about 2% to about 15%, from about 2% to about 12%, from about 2% to about 10%, from about 2% to about 5%, or from about 2% to about 4% by weight based on total weight of the concentrated solution.

In some embodiments, the concentrated cleaning disinfectant comprises gluconic acid in an amount of at least 0.5%, at least 1%, at least 1.5%, or at least 2% by weight; and/or no more than 15%, no more than 12.5%, no more than 10%, no more than 5%, or no more than 3% by weight based on total weight of the concentrated solution.

In some embodiments, the concentrated cleaning disinfectant comprises gluconic acid in an amount of from about 1% to about 15%, from about 1% to about 12.5%, from about 1.5% to about 15%, from about 1.5% to about 12.5%, from about 1.5% to about 10%, from about 1.5% to about 7.5%, from about 1.5% to about 5%, or from about 1.5% to about 3% by weight based on total weight of the concentrated solution.

In some embodiments, the concentrated cleaning disinfectant comprises salicylic acid in an amount of at least 0.1%, at least 0.3%, at least 0.5%, or at least 1% by weight; and/or no more than 5%, no more than 2.5%, or no more than 2% by weight based on total weight of the concentrated solution.

In some embodiments, the concentrated cleaning disinfectant comprises salicylic acid in an amount of from about 0.1% to about 3%, from about 0.1% to about 2.5%, from about 0.1% to about 2%, from about 0.3% to about 3%, from about 0.3% to about 2.5%, or from about 0.3% to about 2% by weight based on total weight of the concentrated solution.

In some embodiments, the antimicrobial acid comprises such synergistic combination wherein a weight ratio of (i) gluconic acid, derivative of gluconic acid, or a combination thereof; and (ii) salicylic acid, derivative of salicylic acid, or a combination thereof is from about 3:1 to about 5:1.

Surface Cleaning Acid

The term "surface cleaning acid' refers to an acidic cleaning agent capable of effectively removing soils that are deposited on the surfaces to be cleaned. The soils may be organic soil, inorganic soil, or a combination thereof.

The surface cleaning acid comprises at least one acid selected from mineral acid, methane sulfonic acid, formic acid, or sulfonic acid having an alkyl group with no greater than three carbon atoms.

The term "mineral acid", as used herein, refers to any acid derived from inorganic compound. Non-limiting examples of mineral acids are phosphoric acid, sulfuric acid, nitric acid, hydrochloric acid, hydrofluoric acid, hydrobromic acid, hydroiodic acid, boric acid, fluoroboric acid, hexafluorosilicilic acid, or hexafluorophosphoric acid.

In some embodiments, the surface cleaning acid comprises phosphoric acid, nitric acid, sulfuric acid, methane sulfonic acid, hydrochloric acid, formic acid, or any combination thereof.

In some embodiments, the concentrated cleaning disinfectant solution comprises the surface cleaning acid in an amount of at least 5%, at least 7%, at least 10%, at least 15%, at least 18%, or at least 20% by weight; and/or no more than 60%, no more than 50%, no more than 40%, or no more than 30% by weight based on total weight of the concentrated solution.

In some embodiments, the concentrated cleaning disinfectant solution comprises the surface cleaning acid in an amount of about 5% to about 60%, about 5% to about 50%, about 5% to about 40%, about 5% to about 30%, from about 7% to about 30% by weight, or from about 18% to about 26% by weight based on total weight of the concentrated solution.

In certain embodiments, the surface cleaning acid comprises a phosphoric acid in an amount of from about 5% to about 30%, from about 10% to about 30%, from about 15% to about 30%, or from about 17.5% to about 25.5% by weight based on total weight of the concentrated cleaning disinfectant solution.

In other preferred embodiments, the surface cleaning acid comprises methane sulfonic acid in an amount of up to 10% by weight, or up to 7.5% by weight on total weight of the concentrated cleaning disinfectant solution.

Solubilizing Agent

The term "solubilizing agent", as used herein, refers to an agent that increases the solubility of one or more of the ingredients in the disclosed cleaning disinfectant solution. A solubilizing agent prevents ingredients in the concentrated cleaning disinfectant solution from precipitating out of the solution at freezing temperatures, thereby allowing the concentrated solution to remain stable at freezing temperatures.

Suitable solubilizing agents may include, but are not limited to, propylene glycol, butylene glycol, hexylene glycol, polyethylene glycol, polysorbate-20, polysorbate-40, isoceteth-15, isoceteth-20, isoceteth-30, sorbeth-20, sorbeth-40, PEG-40 castor oil, polypropylene glycol-5 ceteth 20, or any combination thereof.

In some embodiments, the solubilizing agent includes propylene glycol n-propyl ether (PNP), dipropylene glycol methyl ether (DPM), ethylene glycol monobutyl ether (EGBE), or any combination thereof.

The solubilizing agent may be included in the concentrated cleaning disinfectant solution in an effective amount that ingredients in the concentrated solution do not precipitate out of the solution at freezing temperatures. The effective amount may depend upon the types of solubilizing agents used in the cleaning disinfectant solution.

In some embodiments, the total amount of solubilizing agent in the concentrated cleaning disinfectant solution is at least 0.1%, at least 0.5%, at least 1%, at least 2%, at least 5%, or at least 10% by weight; and/or no more than 25%, no more than 20%, no more than 15%, or no more than 10% by weight based on total weight of the concentrated solution.

In some embodiments, the total amount of solubilizing agent is from about 0.1% to about 25%, from about 0.2% to about 20%, or from about 0.3% to about 13% by weight based on total weight of the concentrated solution. In some embodiments, the total amount of solubilizing agent may be from about 0.5% to about 15%, from about 1% to about 13%, from about 2% to about 13%, or from about 2.3% to about 7.5% by weight based on total weight of the concentrated solution.

In certain embodiments, the solubilizing agent comprises (i) propylene glycol n-propyl ether (PNP), and (ii) at least one of dipropylene glycol methyl ether (DPM) and ethylene glycol monobutyl ether (EGBE).

In certain embodiments, the solubilizing agent comprises propylene glycol n-propyl ether (PNP) in an amount of from about 0.5% to about 10%, from about 0.5% to about 5%, from about 0.75% to about 8%, or from about 0.75% to about 5% by weight based on total weight of the concentrated solution. Still further pursuant to these embodiments, dipropylene glycol methyl ether (DPM) is included along the PNP, wherein DPM is present in an amount of from about 0.5% to about 10%, from about 1% to about 7%, from about 1.5% to about 7%, or from about 1.5% to about 5% based on total weight of the concentrated solution.

In certain embodiments, the solubilizing agent comprises propylene glycol n-propyl ether (PNP) in an amount of from about 0.5% to about 10%, from about 0.5% to about 5%, from about 0.75% to about 8%, or from about 0.75% to about 5% by weight based on total weight of the concentrated solution. Still further pursuant to these embodiments, ethylene glycol monobutyl ether (EGBE) is included along the PNP, wherein EGBE is present in an amount of up to 10%, up to 8%, up to 7.5%, up to 5%, or up to 2.5% by weight based on total weight of the concentrated solution.

In certain embodiments, the solubilizing agent comprises dipropylene glycol methyl ether (DPM) in an amount of from about 1.5% to about 7% by weight based on total weight of the concentrated solution.

In certain embodiments, the solubilizing agent comprises dipropylene glycol methyl ether (DPM) and propylene glycol n-propyl ether (PNP), wherein the weight ratio of DPM to PNP is less than 3, preferably less than 2.5, more preferably less than 2.3. Preferably, the weight ratio of DPM to PNP is from about 1.6 to about 2.3.

In certain embodiments, the solubilizing agent comprises ethylene glycol monobutyl ether (EGBE) in an amount of from about 1% to about 8% by weight based on total weight of the concentrated solution.

In certain embodiments, the solubilizing agent comprises ethylene glycol monobutyl ether (EGBE) and propylene glycol n-propyl ether (PNP), wherein the weight ratio of EGBE to PNP is less than 3, preferably less than 2.5, more preferably less than 2.3. Preferably, the weight ratio of EGBE to PNP is from about 1.6 to about 2.3.

Hydrotrope

The processing conditions, such as temperature, pH, water hardness, and other parameters may vary over a wide range during the cleaning and disinfecting processes. The cleaning disinfectant solution may become unstable under such varying process conditions. For example, the ionic strength and/or water hardness may significantly increase during the operation, resulting in a reduction or loss of relevant properties like emulsion stability, film forming properties, and dispersing capacity. Such instability is undesirable with respect to the cleaning/disinfecting process.

Hydrotrope may maximize the solubility of hydrophobic components in the cleaning disinfectant solution under varying operating conditions. The hydrotrope may be any suitable ionic surfactant, non-ionic surfactant, Gemini emulsifier, or amphotropic surfactant, individually and in the form of mixtures of different surfactants. Suitable hydrotropes may include, but not limited to, alkoxylated fatty alcohols, alkylated polyglycol ethers, alkylated carboxylic acids, sodium sulfonates, fatty acid amides, synthetic sulfonates, non-ionic ethoxylates, or the like.

In some embodiments, the concentrated cleaning disinfectant solution comprises hydrotrope in an amount of at least 0.5%, at least 1%, at least 2%, or at least 3.5% by weight; and/or no more than 10%, no more than 7.5%, no more than 5%, or no more than 4.5% by weight based on total weight of the concentrated solution.

In some embodiments, the hydrotrope is present in an amount of from about 0.5% to about 10%, from about 1% to about 7.5%, from about 2% to about 5%, or from about 3.5% to about 4.5% by weight based on total weight of the concentrated cleaning disinfectant solution.

In some embodiments, hydrotrope comprises sulfonic acid, derivative of sulfonic acid, phosphoric acid, derivative of phosphoric acid, or any combination thereof.

As non-limiting examples, a derivative of sulfonic acid may include a salt of cumene sulfonic acid such as cumene sulfonate sodium salt; a salt of p-menth-6-ene-2-sulfonic acid; a salt of p-menth-1-ene-7-sulfonic acid; a salt of toluol-4-sulfonic acid; or any combination thereof. Other non-limiting examples of derivatives of sulfonic acid include the derivatives of p-toluenesulfonic acid, methanesulfonic acid, benzenesulfonic acid, propane-1-sulfonic acid, hexadecane-1-sulfonic acid, butane-2-sulfonic acid, or any combination thereof.

In certain embodiments, the hydrotrope comprises aromatic sulfonate that includes cumene sulfonate salt such as sodium cumene sulfonate; xylene sulfonate salt such as sodium xylene sulfonate; or a mixture thereof.

In some embodiments, the hydrotrope comprises derivative of sulfonic acid in an amount of from about 3.5% to about 4.5% by weight based on total weight of the concentrated solution.

As non-limiting examples, a derivative of phosphoric acid includes tris(2-ethylhexyl)phosphate, 2-ethylhexylphosphate, dibutyl hydrogen phosphate, tributyl hydrogen phosphate, bis(2-ethylhexyl) hydrogen phosphate, amino-tris-methylenephosphonic acid (ATMP), or 1-hydroxyethylidene-1,1-diphosphonic acid (HEDP).

Surfactant

Surfactant may perform any combination of wetting the surface to be cleaned, loosening deposited soils at the surface, and emulsifying the soils removed from the surface to keep the soils suspended in the cleaning disinfectant solution. In the disclosed cleaning disinfectant solution, cleansing is provided, at least in part, by surfactant.

The concentrated cleaning disinfectant solution comprises an anionic surfactant, a non-ionic surfactant, or a mixture thereof. In some embodiments, the surfactant used in the disclosed cleaning disinfectant solution is allowed to be ingested.

In some embodiments, the concentrated cleaning disinfectant solution comprises surfactant in an amount of from about 0.1% to about 10%, from about 0.2% to about 7.5%, or from about 0.25% to 5% by weight based on total weight of the concentrated solution.

In certain embodiments, the anionic surfactant comprises polyoxyethylene alkyl ether carboxylic acid, salt thereof, or a combination thereof. Further pursuant to these embodiments, the polyoxyethylene alkyl ether carboxylic acid comprises capryleth-6 carboxylic acid. Still further pursuant to these embodiments, the capryleth-6 carboxylic acid is present in an amount of from about 0.1% to about 2.5%, or from about 0.25% to about 1% by weight based on total weight of the concentrated cleaning disinfectant solution.

In some embodiments, the non-ionic surfactant comprises alkylene oxide modified Guerbet alcohol, fatty alcohol alkoxylate, or a mixture thereof.

The Guerbet alcohol is represented by the following general formula (1),

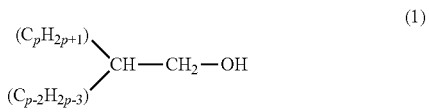

wherein p is an integer between 4 and 14.

In some embodiments, the non-ionic surfactant comprises alkylene oxide modified Guerbet alcohol. In certain embodiments, the alkylene oxide modified Guerbet alcohol comprises an oxirane, 2-methyl-, polymer with oxirane, mono (2-propylheptyl) ether, such as LUTENSOL® XL 80 product commercially available from BASF Corporation. Further pursuant to these certain embodiments, the alkylene oxide modified Guerbet alcohol is present in an amount of no more than 5%, no more than 4%, no more than 3%, or no more than 2% by weight based on total weight of the concentrated cleaning disinfectant solution.

In some embodiments, the fatty alcohol alkoxylate surfactant may comprise C12-C15 linear ethoxylated alcohol, C12-C15 branched ethoxylated alcohol, C12-C15 linear propoxylated alcohol, C12-C15 branched propoxylated alcohol, or any combination thereof. A non-limiting example of fatty alcohol alkoxylate surfactant includes PLURAFAC® LF 403 product commercially available from BASF Corporation.

In some embodiments, the concentrated cleaning disinfectant solution further comprise a co-surfactant.

The term "co-surfactant", as used herein, refers to a surfactant that is used in combination with one or more primary surfactants, e.g., to improve the emulsification of the ingredients in the solution. Typically, the co-surfactant represents a lower percent by weight, compared to the surfactant in the concentrated cleaning disinfectant solution.

In some embodiments, the concentrated cleaning disinfectant solution comprises co-solvent in an amount of up to 5% by weight based on total weight of the concentrated solution. In certain embodiments, the co-surfactant is present in an amount of from about 0.05% to about 2%, from about 0.1% to about 1%, from about 0.25% to about 7.5% by weight based on total weight of the concentrated solution.

In some embodiments, the co-surfactant comprises polyoxyethylene octyl ether carboxylic acid, such as AKYPO® LF1 product commercially available from Kao Global Chemicals.

Concentrated Cleaning Disinfectant Solution

The disclosed concentrated cleaning disinfectant solution is stable at freezing temperatures, and comprises:
  antimicrobial acid comprising a synergistic combination of (i) gluconic acid, derivative of gluconic acid, or a combination thereof and (ii) salicylic acid, derivative of salicylic acid, or a combination thereof;
  surface cleaning acid comprising at least one acid selected from mineral acid, methane sulfonic acid, formic acid, or sulfonic acid having an alkyl group with no greater than three carbon atoms;
  solubilizing agent;
  hydrotrope; and
  surfactant selected from anionic surfactant, non-ionic surfactant, or a mixture thereof.

In some embodiments, the concentrated cleaning disinfectant solution is substantially free of hydrogen peroxide and/or any other carboxylic acid, e.g. fumaric acid, citric acid, lactic acid, oxalic acid, maleic acid, acetic acid, tartaric acid, malic acid, succinic acid, propionic acid, glycolic acid, benzoic acid, and the like.

In some embodiments, the concentrated cleaning disinfectant solution may have pH in a range of about 0.5 to about 2.0.

In some embodiments, the concentrated cleaning disinfectant solution comprises:
from about 2% to about 5% by weight of the antimicrobial acid;
from about 5% to about 40% by weight of the surface cleaning acid;
from about 0.5% to about 15% by weight of the solubilizing agent;
from about 3.5% to about 4.5% by weight of the hydrotrope; and
from about 0.25% to about 5% by weight of the surfactant, all based on total weight of the concentrated solution.

In some embodiments, the concentrated cleaning disinfectant solution further comprise aqueous-based solvent, co-surfactant, foaming agent, foam stabilizer, coloring agent, viscosity modifying agent, thickener, gelling agent, pH controlling agent, water softening agent, chelating agent, preservative, or any combination thereof.

Aqueous-based Solvent

The term "aqueous-based solvent", as used herein, refers to a solvent system comprising water as one component. In some embodiments, water is the only component in the aqueous-based solvent. In other embodiments, the aqueous-based solvent comprises water and at least one other solvent that exhibits good solubility in water. Non-limiting examples of such other solvents are ethylene glycol, n-propyl glycol, isopropanol, ethanol, or methanol.

The concentrated cleaning disinfectant solution may comprise aqueous-based solvent in an amount of from about 40% to about 89%, from about 50% to about 75%, from about 55% to about 70%, or from about 55% to about 60% by weight based on total weight of the concentrated solution.

In some embodiments, the concentrated cleaning disinfectant solution is substantially free of hydrophobic solvent, which is defined herein as a solvent that exhibits a solubility in water from 0 to about 20 ml per 100 ml of water. Examples of hydrophobic solvents include, but not limited to, mineral spirits, propylene glycol phenyl ether, or ethylene glycol phenyl ether.

The disclosed disinfecting cleaning disinfectant solutions provide a good cleaning performance, as well as a broad spectrum of disinfecting performance with excellent efficacy at a reduced concentration. Furthermore, the disclosed cleaning disinfectant solutions remain stable even upon being exposed to low temperatures, such as temperatures at or below freezing.

Method of Cleaning and Disinfecting Surface

The method of cleaning and disinfecting a surface, comprises producing a diluted cleaning disinfectant solution from the disclosed concentrated cleaning disinfectant solution; and contacting the surface with the diluted cleaning disinfectant solution.

In some embodiments, the diluted cleaning disinfectant solution comprises at least 0.1%, at least 0.25%, at least 0.5%, at least 0.75%, at least 1%, at least 2%, at least 2.5%, at least 5%, or at least 10% by weight of the disclosed concentrated cleaning disinfectant solution based on total weight of the diluted solution.

In some embodiments, the diluted cleaning disinfectant solution comprises up to 5% or up to 10% by weight of the disclosed concentrated cleaning disinfectant solution based on total weight of the diluted solution.

In certain embodiments, the diluted cleaning disinfectant solution comprises from about 0.5% to about 5% by weight of the concentrated cleaning disinfectant solution based upon total weight of the diluted solution.

In certain embodiments, the diluted cleaning disinfectant solution comprises about 1% by weight of the concentrated cleaning disinfectant solution based upon total weight of the diluted solution cleaner.

In some embodiments, the disclosed method of cleaning and disinfecting a surface further comprises removing gross or large debris from the surface, prior to contacting the surface with the diluted cleaning disinfectant solution.

In the disclosed method of cleaning and disinfecting, the diluted cleaning disinfectant is allowed to contact with the surface to be cleaned for a sufficient time to remove soils on the surface. In some embodiments, the method comprises contacting the surface with the diluted cleaning disinfectant for at least 5 minutes.

In some embodiments, the disclosed method for cleaning and disinfecting further comprises rinsing the surface with water to remove any residue cleaning disinfectant solution from the surface.

In some embodiments, the surface to be cleaned by the disclosed cleaning disinfectant solution comprises surface of industrial process equipment, or food contact surface, or both. Non-limiting examples of the industrial process equipment includes tank and associated piping. The industrial process equipment may be a food manufacturing process or a beverage manufacturing process.

In some embodiments, the disclosed method of cleaning and disinfecting a surface is a clean-in-place method.

In some embodiments, the disclosed method of cleaning and disinfecting provides an antimicrobial efficacy that meets the requirements of Biocidal Product Registration (BPR) standard EN1276 test method, EN1650 test method, or both. The BPR standard EN1276 microbial testing procedure requires a log reduction of greater than or equal to 5 in five minutes of contacting the surface with the disinfectant at 20° C. The BPR standard EN 1650 microbial testing procedure requires a log reduction of greater than or equal to 4 in fifteen minutes of contacting the surface with the disinfectant at 20° C.

The disclosed method provides good cleaning performance for removal of soil from a surface. Various soil types are effectively removed from the surface, including the soils most likely to be encountered in normal cleaning operation. The disclosed method shows excellent cleaning ability for a food contact surface, wherein the soil is typically a blend of protein, starch and lipids. Using a Gardner test, the disclosed method provides comparable cleaning performance to a method using conventional cleaning solution.

The disclosed method provides an enhanced antimicrobial efficacy against various microorganisms, such as bacteria, yeasts, fungi, spores, viruses, etc. See EXAMPLES 1 and 2 for yeast *Saccharomyces cerevisiae*; EXAMPLE 2 for bacteria *Staphylococcus aureus*, *Escherichia coli*, and *Lactobacillus brevis*; EXAMPLE 2 for fungus *Aspergillus niger*.

The enhanced antimicrobial efficacy is, at least, due to the unexpected synergistic effect of antimicrobial acid, which is a combination of (i) gluconic acid, derivative of gluconic acid, or a combination thereof; and (ii) salicylic acid, derivative of salicylic acid, or a combination thereof. See EXAMPLE 1. Due to this unexpected synergistic effect, the required amount of antimicrobial acid in the disclosed cleaning disinfectant solution is substantially lower than the amount required in the conventional cleaning disinfectant solution. See EXAMPLE 2. The required amount of salicylic acid in the conventional cleaning disinfectant solution is in a range of 2% to 10% by weight based on total weight of the solution. On the other hands, the required amount of salicylic acid in the disclosed cleaning disinfectant solution is less than 2% by weight based on total weight of the solution, due to the synergistic antimicrobial effect when used in combination with gluconic acid. See TABLE 4.

Furthermore, the concentrated cleaning disinfectant solution used in the present method remains stable across a broad range of temperatures that can be experienced during transportation and storage. The concentrated cleaning disinfectant solution remains stable even upon being exposed to low temperatures, such as temperatures at or below freezing point. See EXAMPLES 3-5.

Salicylic acid has been known to crystallize out of the concentrated cleaning disinfectant solution at or below 0° C. Therefore, typically organic solvent such as diglycol in an amount of 15% to 75% by weight is required to prevent salicylic acid from crystallizing from the concentrated cleaning disinfectant solution.

Unexpectedly, the concentrated cleaning disinfectant solution of present disclosure shows excellent stability even at freezing temperatures. This is achieved by using a specific mixture of solubilizing agents. See EXAMPLES 3-5.

The following non-limiting examples illustrate representative cleaning disinfectant solutions of the present disclosure and methods of using thereof.

EXAMPLES

Materials

Fatty alcohol alkoxylate was Plurafac® LF 403 low-foaming, non-ionic surfactant commercially available from BASF Corporation. Polyoxyethylene octyl ether carboxylic acid was Akypo® LF1 solvent from Kao Chemicals. Alkylene oxide modified Guerbet alcohol was an oxirane, 2-methyl-, polymer with oxirane, mono(2-propylheptyl) ether commercially available as Lutensol® XL 80 non-ionic surfactant from BASF Corporation. Ethylene glycol monobutyl ether was Butyl CELLOSOLVE™ solvent commercially available from Dow Chemical Company.

Determination of Antimicrobial Efficacy

A Zone of Inhibition Test (also known as the Kirby-Bauer Test, Antimicrobial Susceptibility Test, Disk Diffusion Test, or Agar Well Diffusion Test) was used to determine the antimicrobial efficacy of the cleaning disinfectant solution against the tested microorganisms.

The tested microorganisms were smeared evenly onto the surface of an agar plate. Next, a well of 10 mm was made in agar with sterile cork borer. The well was filled with the test cleaning disinfectant solution, Then, the plate was incubated, As the microorganisms grew on the surface of the plate, the tested cleaning disinfectant solution diffused from the well out into the agar. The concentration of tested solution in the agar decreased as the tested solution diffused further from the well. Eventually, the concentration of tested solution in the agar dropped below the level that needed to inhibit the growth of microorganisms.

The zone of inhibition was reported herein as the diameter (in millimeter unit) of circular area around the well in which the concentration of cleaning disinfectant solution was high enough to inhibit the growth of tested microorganisms.

Antimicrobial efficacy of the tested cleaning disinfectant solution (in percentage, %) was calculated using the following equation:

$$\% \text{ Antimicrobial Efficacy} = \frac{(Z_1 - Z_0) \times 100}{Z_0},$$

wherein
$Z_0$ was the zone of inhibition for a solution containing no antimicrobial acid, and
$Z_1$ was the zone of inhibition for the tested cleaning disinfectant solution.

EXAMPLE 1

Synergistic Effect of Antimicrobial Acids

Five cleaning disinfectant solutions (Solutions #1 to #5) were prepared, each comprising the ingredients as shown in TABLE 1.

TABLE 1

| Ingredients | Solution | | | | |
|---|---|---|---|---|---|
| (% weight) | #1 | #2 | #3 | #4 | #5 |
| Salicylic acid | — | 0.3 | — | 0.3 | 0.8 |
| Gluconic acid | — | — | 1.5 | 1.5 | 3.0 |
| Phosphoric acid | 25.5 | 25.5 | 25.5 | 25.5 | 21.3 |
| Dipropylene glycol methyl ether (DPM) | 1.6 | 1.6 | 1.6 | 1.6 | 5.0 |
| Propylene Glycol n-propyl Ether (PNP) | 0.8 | 0.8 | 0.8 | 0.8 | 2.3 |
| Sodium cumene sulfonate | 4.4 | 4.4 | 4.4 | 4.4 | 4.4 |
| Fatty alcohol alkoxylate | 3.0 | 3.0 | 3.0 | 3.0 | 3.0 |
| Alkylene oxide modified Guerbet alcohol | 2.0 | 2.0 | 2.0 | 2.0 | 2.0 |
| Water | q.s. 100 | | | | |

TABLE 2 showed the antimicrobial efficacy of the cleaning disinfectant solutions #1 to #5 against yeast *Saccharomyces cerevisiae*, based on the agar well diffusion test method.

TABLE 2

| Solution | Antimicrobial Acid | Zone of Inhibition (mm) | % Antimicrobial Efficacy |
|---|---|---|---|
| #1 | None | 15 | — |
| #2 | 0.3 wt % Salicylic Acid | 16 | 7% |
| #3 | 1.5 wt % Gluconic Acid | 18 | 20% |
| #4 | 0.3 wt % Salicylic Acid 1.5 wt % Gluconic Acid | 23 | 53% |
| #5 | 0.8 wt % Salicylic Acid 3.0 wt % Gluconic Acid | 30 | 100% |

Solution #2, which contained 0.3 wt % salicylic acid but no gluconic acid, provided an antimicrobial efficacy of 7% against *S. cerevisiae*. Solution #3, which contained 1.5 wt % gluconic acid but no salicylic acid, provided an antimicrobial efficacy of 20% against *S. cerevisiae*. Solution #4, which contained 0.3 wt % salicylic acid and 1.5 wt % gluconic acid, provided an antimicrobial efficacy of 53% against *S. cerevisiae*. Solution #5, which contained 0.8 wt % salicylic acid and 3.0 wt % gluconic acid, provided an antimicrobial efficacy of 100% against *S. cerevisia*.

If the antimicrobial effect between salicylic acid and gluconic acid was merely an additive effect, the expected antimicrobial efficacy of Solution #3 would be 27% (i.e., 7%+20%) against *S. cerevisiae*. However, Solution #3 showed an antimicrobial efficacy of 53% against *S. cerevisiae*, which was about two times higher than the expected value. Therefore, there was a synergistic effect between salicylic acid and gluconic acid.

EXAMPLE 2

Antimicrobial Efficacy of Cleaning Disinfectant Solution

Solution #5 was diluted with water at three different concentrations. As shown in TABLES 3A and 3B, the first diluted solution contained 0.5 wt % of Solution #5 based on total weight of the diluted solution. Likewise, the second and third dilute solutions contained 1.0 wt % and 1.5 wt % of Solution #5, respectively.

TABLE 3A showed the test results against bacteria *Staphylococcus aureus, Escherichia coli*, and *Lactobacillus brevis* according to the EN 1276:2009 test protocols with a contact time of 30 minutes, under clean or dirty conditions at 25° C. or 4° C., at varying concentrations of Solution #5. To pass the EN1276 test method, a log reduction of greater than or equal to 5 must be achieved in five minutes.

TABLE 3A

| Microorganism | Amount (wt %) of Solution #5 in the Tested Solution | EN1276: 2009 Test Method | | | |
|---|---|---|---|---|---|
| | | Clean Condition | | Dirty Condition | |
| | | 25° C. | 4° C. | 25° C. | 4° C. |
| Staphylococcus aureus | 0.5 | Pass | Pass | Pass | Fail |
| | 1.0 | Pass | Pass | Pass | Pass |
| | 1.5 | Pass | Pass | Pass | Pass |
| Escherichia coli | 0.5 | Pass | Pass | Pass | Pass |
| | 1.0 | Pass | Pass | Pass | Pass |
| | 1.5 | Pass | Pass | Pass | Pass |
| Lactobacillus brevis | 0.5 | Pass | Fail | Pass | Fail |
| | 1.0 | Pass | Pass | Pass | Pass |
| | 1.5 | Pass | Pass | Pass | Pass |

TABLE 3B showed the test results against fungus *Aspergillus niger* and yeast *Saccharomyces cerevisiae* according to the EN1650:2008 test protocol with a contact time of 30 minutes, under clean or dirty conditions at 25° C. or 4° C., at varying concentrations of Solution #5. To pass the EN 1650:2008 antimicrobial testing protocol, a log reduction of greater than or equal to 4 must be achieved in fifteen minutes.

TABLE 3B

| Microorganism | Amount (wt %) of Solution #5 in the Tested Solution | EN 1650: 2008 Test Method | | | |
|---|---|---|---|---|---|
| | | Clean Condition | | Dirty Condition | |
| | | 25° C. | 4° C. | 25° C. | 4° C. |
| Aspergillus niger | 1.5 | Fail | Fail | Fail | Fail |
| | 2.0 | Pass | Fail | Fail | Fail |
| | 2.5 | Pass | Pass | Pass | Pass |
| Saccharomyces cerevisiae | 1.5 | Fail | Fail | Fail | Fail |
| | 2.0 | Pass | Pass | Fail | Fail |
| | 2.5 | Pass | Pass | Pass | Pass |

TABLES 3A and 3B showed that the antimicrobial levels passing the EN 1276:2009 and EN 1650:2008 test protocols were achieved even at lower temperatures down to about 4° C. at an appropriate concentration level of Solution #5.

TABLE 4 summarized the amount (ppm) of each antimicrobial acid (salicylic acid, gluconic acid) required in the cleaning disinfectant solution in order to achieve the desired antimicrobial levels that passed the EN1276:2009 and EN1650:2008 test methods.

TABLE 4

| Activity | Soil Condition | Temperature | Concentration of Antimicrobial Acids, ppm | |
|---|---|---|---|---|
| | | | Gluconic Acid | Salicylic Acid |
| Antibacterial | Clean | 25° C. | 150 | 37 |
| | | 4° C. | 300 | 75 |
| | Dirty | 25° C. | 150 | 37 |
| | | 4° C. | 300 | 75 |
| Antifungal | Clean | 25° C. | 600 | 150 |
| | | 4° C. | 750 | 188 |
| | Dirty | 25° C. | 750 | 188 |
| | | 4° C. | 750 | 188 |

Solution #5, contained a synergistic combination of 0.8 wt % salicylic acid and 3 wt % gluconic acid, provided an enhanced level of antimicrobial efficacy. Due to this synergistic effect, the required amount of antimicrobial acid in Solution #5 was substantially lower than the amount required in the conventional cleaning disinfectant solution.

Conventionally, the required amount of salicylic acid in the cleaning disinfectant solution must be in a range of 2 wt % to 10 wt % based on total weight of the solution, in order to achieve the desired antimicrobial levels that passed the EN1276:2009 and EN1650:2008 test methods. Here, the required amount of salicylic acid in the disclosed cleaning disinfectant solution could be much less than 2 wt % due to the synergistic antimicrobial effect when used in combination with gluconic acid.

EXAMPLE 3

Effect of Solubilizing Agents on Stability

Five cleaning disinfectant solutions (Solutions #6 to #10) were prepared, each comprising the ingredients as shown in TABLE 5. Three solubilizing agents (propylene glycol methyl ether, ethylene glycol monobutyl ether, propylene glycol n-propyl ether) were tested for their effects on the stability of the solutions.

TABLE 5

| Ingredients (% weight) | Solution | | | | |
|---|---|---|---|---|---|
| | #6 | #7 | #8 | #9 | #10 |
| Salicylic acid | 1.9 | 1.9 | 0.3 | 0.8 | 0.8 |
| Gluconic acid | — | — | 1.5 | 3.0 | 3.0 |
| Phosphoric acid | 17.9 | 17.9 | 25.5 | 21.3 | 21.3 |
| Dipropylene glycol methyl ether (DPM) | — | — | 1.6 | 5.0 | 5.0 |
| Ethylene glycol monobutyl ether (EGBE) | 8.0 | 8.0 | — | — | — |
| Propylene glycol n-propyl ether (PNP) | 2.2 | 5.0 | 0.8 | 2.3 | 2.0 |
| Sodium cumene sulfonate | 4.0 | 3.6 | 4.4 | 4.4 | 4.4 |
| Alkylene oxide modified Guerbet alcohol | — | — | 2.0 | 2.0 | 2.0 |
| Fatty alcohol alkoxylate | — | — | 3.0 | 3.0 | 3.0 |
| Polyoxyethylene octyl ether carboxylic acid | 0.5 | 0.5 | — | — | — |
| Water | q.s. 100 | | | | |

Solutions #6 to #10 were tested for stability by subjecting to a specific temperature for an extended period of time to determine whether crystallization occurred. TABLE 6 showed the results of the stability testing.

TABLE 6

| | Solution | | | | |
|---|---|---|---|---|---|
| | #6 | #7 | #8 | #9 | #10 |
| Ratio by Weight of the Solubilizing Agents | | | | | |
| DPM to PNP | — | — | 2.0 | 2.2 | 2.5 |
| EGBE to PNP | 3.6 | 1.6 | — | — | — |
| Stability at Temperature | | | | | |
| 50° C. | stable | stable | stable | stable | stable |
| 25° C. | stable | stable | stable | stable | stable |
| 0° C. | crystallized | stable | stable | stable | crystallized |
| −25° C. | crystals | stable | stable | stable | crystals |

Solution #6 with the weight ratio of DPM to PNP stabilizers of 3.6 was unstable (crystallized) at the temperature of 0° C. or below. Solution #7 with the weight ratio of DPM to PNP stabilizers of 1.6 was stable even at the temperature as low as −25° C.

Solutions #8 and #9 with the weight ratios of EGBE to PNP stabilizers of 2.0 and 2.2 were stable even at the temperature as low as −25° C. Yet, Solution #10 with the weight ratio of EGBE to PNP stabilizers of 2.5 was unstable (crystallized) at the temperature of 0° C. or below.

EXAMPLE 4

Solutions #11 to #14 were prepared, each comprising the ingredients as shown in TABLE 7. Each of Solutions #11 to #14 contained DPM and PNP as stabilizers, wherein the weight ratio of DPM:PNP was 2.2. Four mineral acids were tested: nitric acid, sulfuric acid, methane sulfonic acid, and formic acid.

TABLE 7

| Ingredients | Solution | | | |
|---|---|---|---|---|
| (% weight) | #11 | #12 | #13 | #14 |
| Salicylic acid | 0.8 | 0.8 | 0.8 | 0.8 |
| Gluconic acid | 3.0 | 3.0 | 3.0 | 3.0 |
| Nitric acid | — | — | — | 20.5 |
| Sulfuric Acid | 20.6 | — | — | — |
| Methane Sulfonic acid | — | 21.0 | — | — |
| Formic Acid | — | — | 20.8 | — |
| Dipropylene glycol methyl ether (DPM) | 5.0 | 5.0 | 5.0 | 5.0 |
| Propylene glycol n-propyl ether (PNP) | 2.3 | 2.3 | 2.3 | 2.3 |
| Sodium cumene sulfonate | 4.4 | 4.4 | 4.4 | 4.4 |
| Alkylene oxide modified Guerbet alcohol | 0.5 | 1.0 | 1.0 | 1.0 |
| Fatty alcohol alkoxylate | — | 1.5 | 1.5 | 1.5 |
| Polyoxyethylene octyl ether carboxylic acid | 0.3 | 0.3 | 0.3 | 0.3 |
| Water | q.s. 100 | | | |

As shown in TABLE 8, Solutions #11 to #14 (each with the weight ratio of DPM:PNP stabilizing agents of 2.2) were stable even at the temperature as low as −15° C., regardless the types of mineral acids.

TABLE 8

| | Solution | | | |
|---|---|---|---|---|
| Temperature | #11 | #12 | #13 | #14 |
| 50° C. | stable | stable | stable | stable |
| 25° C. | stable | stable | stable | stable |
| 0° C. | stable | stable | stable | stable |
| −15° C. | stable | stable | stable | stable |

EXAMPLE 5

Solution #15 was prepared, comprising the ingredients shown in TABLE 11. The solution contained DPM and PNP as stabilizers, wherein the weight ratio of DPM:PNP was 2.2 and sodium xylene sulfonate as hydrotrope. The stability test showed that Solution #15 was stable even at freezing temperatures. This stability of Solution #15 has been demonstrated to be similar to those solutions having sodium cumene sulfonate as hydrotrope. Thus, these results for Solution #15 show that other sulfonates may also lead to the stability of the formulation.

TABLE 11

| Ingredients | Weight (%) |
|---|---|
| Water | 58.3 |
| Salicylic acid | 0.8 |
| Gluconic acid | 3.0 |
| Methane sulfonic acid | 21.3 |
| Dipropylene glycol methyl ether (DPM) | 5.0 |
| Propylene Glycol n-propyl Ether (PNP) | 2.3 |
| Sodium xylene sulfonate | 4.4 |
| Fatty alcohol alkoxylate | 3.0 |
| Alkylene oxide modified Guerbet alcohol | 2.0 |

Various features and advantages of the invention are set forth in the following claims.

We claim:

1. A method of cleaning and disinfecting a surface, comprising:
    producing a diluted cleaning disinfectant solution from a concentrated cleaning disinfectant solution that is stable at a freezing temperature; and
    contacting the surface with the diluted cleaning disinfectant solution;
    wherein the concentrated cleaning disinfectant solution comprises:
        antimicrobial acid comprising a synergistic combination of (i) gluconic acid, derivative of gluconic acid, or a combination thereof and (ii) salicylic acid, derivative of salicylic acid, or a combination thereof;
        surface cleaning acid comprising at least one acid selected from mineral acid, methane sulfonic acid, formic acid, or sulfonic acid having an alkyl group with no greater than three carbon atoms; and
        surfactant selected from anionic surfactant, non-ionic surfactant, or a mixture thereof.

2. The method of claim 1, wherein the antimicrobial acid in the concentrated solution fulfills at least one of the following:
    (a) the antimicrobial acid is present in an amount of 1% to about 15% by weight based on total weight of the concentrated solution;
    (b) a weight ratio of (i) gluconic acid, derivative of gluconic acid, or a combination thereof; and (ii) salicylic acid, derivative of salicylic acid, or a combination thereof in the antimicrobial acid is from about 3:1 to about 5:1.

3. The method of claim 1, wherein the surface cleaning acid in the concentrated solution fulfills at least one of the following:
(a) the surface cleaning acid is present in an amount of from about 5% to about 30% by weight based on total weight of the concentrated solution;
(b) the surface cleaning acids comprises phosphoric acid, nitric acid, sulfuric acid, methane sulfonic acid, hydrochloric acid, formic acid, or any combination thereof.

4. The method of claim 1, wherein the concentrated solution further comprises solubilizing agent, and wherein the solubilizing agent fulfills at least one of the following:
(a) the solubilizing agent is present in an amount of from about 0.1% to about 25% by weight based on total weight of the concentrated solution;
(b) the solubilizing agent comprises propylene glycol n-propyl ether, dipropylene glycol methyl ether, ethylene glycol monobutyl ether, or any combination thereof.

5. The method of claim 1, wherein the concentrated cleaning disinfectant solution further comprises hydrotrope, and wherein the hydrotrope fulfills at least one of the following:
(a) the hydrotrope is present in an amount of from about 0.5% to about 10% by weight based on total weight of the concentrated solution;
(b) the hydrotrope comprises a derivative of sulfonic acid.

6. The method of claim 1, wherein the concentrated cleaning disinfectant solution comprises the surfactant from about 0.1% to about 10% by weight based on total weight of the concentrated solution.

7. The method of claim 1, wherein the anionic surfactant fulfills at least one of the following:
(i) the anionic surfactant comprises polyoxyethylene alkyl ether carboxylic acid, salt thereof, or a combination thereof;
(ii) the anionic surfactant comprises capryleth-6 carboxylic acid;
(iii) the anionic surfactant is present in an amount of from about 0.25% to about 1% by weight based on total weight of the concentrated solution.

8. The method of claim 1, wherein the non-ionic surfactant fulfills at least one of the following:
(i) the non-ionic surfactant comprises alkylene oxide modified Guerbet alcohol, fatty alcohol alkoxylate, or a mixture thereof;
(ii) the non-ionic surfactant comprises an oxirane, 2-methyl, polymer with oxirane, mono (2-propylheptyl) ether;
(iii) the non-ionic surfactant comprises alkylene oxide modified Guerbet alcohol acid in an amount of no more than 2% by weight based on total weight of the concentrated solution;
(iv) the non-ionic surfactant comprises fatty alcohol alkoxylate selected from C12-C15 linear ethoxylated alcohol, C12-C15 branched ethoxylated alcohol, C12-C15 linear propoxylated alcohol, C12-C15 branched propoxylated alcohol, or any combination thereof.

9. The method of claim 1, wherein the concentrated cleaning disinfectant solution further comprises co-solvent, and wherein the co-solvent fulfills at least one of the following:
(a) the co-solvent comprises polyoxyethylene octyl ether carboxylic acid;
(b) the co-solvent is present in an amount of up to 5% by weight based on total weight of the concentrated solution.

10. The method of claim 1, wherein the concentrated solution comprises:
from about 2% to about 5% by weight of the antimicrobial acid;
from about 5% to about 40% by weight of the surface cleaning acid;
from about 0.5% to about 15% by weight of a solubilizing agent;
from about 3.5% to about 4.5% by weight of a hydrotrope; and
from about 0.25% to about 5% by weight of the surfactant, all based on total weight of the concentrated solution.

11. The method of claim 1, wherein the method fulfills at least one of the following:
(i) the diluted cleaning disinfectant solution comprises from about 0.5% to about 5% by weight of the concentrated cleaning disinfectant solution based upon total weight of the diluted solution;
(ii) the surface comprises surface of industrial process equipment, or food contact surface, or both.

12. The method of claim 11, wherein the method fulfills at least one of the following:
(a) the method is a clean-in-process method;
(b) the industrial process equipment includes tank and associated piping;
(c) the industrial process equipment is a food manufacturing process, or a beverage manufacturing process.

13. A concentrated cleaning disinfectant solution for cleaning and disinfecting a surface, wherein the concentrated solution is stable at freezing temperatures and comprises:
antimicrobial acid comprising a synergistic combination of (i) gluconic acid, derivative of gluconic acid, or a combination thereof and (ii) salicylic acid, derivative of salicylic acid, or a combination thereof;
surface cleaning acid comprising at least one acid selected from mineral acid, methane sulfonic acid, formic acid, or sulfonic acid having an alkyl group with no greater than three carbon atoms; and
surfactant selected from anionic surfactant, non-ionic surfactant, or a mixture thereof.

14. The concentrated solution of claim 13, comprising:
from about 2% to about 5% by weight of the antimicrobial acid;
from about 5% to about 40% by weight of the surface cleaning acid; and
from about 0.25% to about 5% by weight of the surfactant, all based on total weight of the concentrated solution.

15. A diluted cleaning disinfectant solution obtained from the concentrated cleaning solution of claim 13.

16. A diluted cleaning disinfectant solution obtained from the concentrated cleaning disinfectant solution of claim 14.

17. The method of claim 1, wherein the antimicrobial acid in the concentrated solution fulfills at least one of the following:
(a) the gluconic acid is present in an amount of from about 1% to about 3% by weight based on total weight of the concentrated solution;
(b) the salicylic acid is present in an amount of 0.1% to about 2% by weight based on total weight of the concentrated solution;

(c) the antimicrobial acid consists of the synergistic combination of (i) gluconic acid, derivative of gluconic acid, or a combination thereof and (ii) salicylic acid, derivative of salicylic acid, or a combination thereof.

18. The method of claim 1, wherein the mineral acid comprises phosphoric acid, sulfuric acid, nitric acid, hydrochloric acid, hydrofluoric acid, hydrobromic acid, hydroiodic acid, boric acid, fluoroboric acid, hexafluorosilicilic acid, hexafluorophosphoric acid, or any combination thereof.

19. The method of claim 4, wherein the solubilizing agent in the concentrated solution fulfills at least one of the following:
 (a) the solubilizing agent comprises the propylene glycol n-propyl ether in an amount of from about 0.5% to about 5% by weight based on total weight of the concentrated solution;
 (b) the solubilizing agent comprises the dipropylene glycol methyl ether in an amount of from about 1.5% to about 7% by weight based on total weight of the concentrated solution;
 (c) the solubilizing agent comprises the dipropylene glycol methyl ether and the propylene glycol n-propyl ether, wherein a weight ratio of the dipropylene glycol methyl ether to the propylene glycol n-propyl ether is less than 3;
 (d) the solubilizing agent comprises the ethylene glycol monobutyl ether in an amount of from about 1% to about 8% by weight based on total weight of the concentrated solution;
 (e) the solubilizing agent comprises the ethylene glycol monobutyl ether and the propylene glycol n-propyl ether, wherein a weight ratio of the ethylene glycol monobutyl ether to the propylene glycol n-propyl ether is less than 3.

20. The method of claim 5, wherein the derivative of sulfonic acid fulfills at least one of the following:
 (a) the derivative of sulfonic acid comprises cumene sulfonate salt, xylene sulfonate salt, or a mixture thereof;
 (b) the derivative of sulfonic acid is presented in an amount of from about 3.5% to about 4.5% by weight based on total weight of the concentrated solution.

\* \* \* \* \*